United States Patent
Tang et al.

(10) Patent No.: US 8,263,930 B2
(45) Date of Patent: Sep. 11, 2012

(54) PLATFORM FOR FIELD ASYMMETRIC WAVEFORM ION MOBILITY SPECTROMETRY WITH ION PROPULSION MODES EMPLOYING GAS FLOW AND ELECTRIC FIELD

(75) Inventors: Keqi Tang, Richland, WA (US); Alexandre A. Shvartsburg, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 278 days.

(21) Appl. No.: 12/690,818

(22) Filed: Jan. 20, 2010

(65) Prior Publication Data
US 2010/0207022 A1    Aug. 19, 2010

Related U.S. Application Data

(60) Provisional application No. 61/146,795, filed on Jan. 23, 2009.

(51) Int. Cl.
*H01J 49/40* (2006.01)
(52) U.S. Cl. .................... 250/282; 250/287
(58) Field of Classification Search ........... 250/281–300
See application file for complete search history.

(56) References Cited

U.S. PATENT DOCUMENTS

| | | | |
|---|---|---|---|
| 5,430,359 A | | 7/1995 | Swenson et al. |
| 6,107,628 A * | | 8/2000 | Smith et al. .............. 250/292 |
| 6,512,224 B1 * | | 1/2003 | Miller et al. ............. 250/286 |
| 6,815,669 B1 | | 11/2004 | Miller et al. |
| 7,223,967 B2 | | 5/2007 | Guevremont et al. |
| 7,339,166 B2 * | | 3/2008 | Tang et al. .............. 250/288 |
| 7,456,390 B2 | | 11/2008 | Miller et al. |
| 7,491,930 B2 | | 2/2009 | Shvartsburg et al. |
| 7,498,570 B2 | | 3/2009 | Boyle et al. |
| 7,547,879 B2 | | 6/2009 | Miller et al. |
| 7,550,717 B1 * | | 6/2009 | Belford et al. .......... 250/281 |
| 7,598,488 B2 * | | 10/2009 | Park ....................... 250/290 |
| 2010/0282961 A1 * | | 11/2010 | Miller et al. ............. 250/282 |

OTHER PUBLICATIONS

Purves, Randy W. et al., Electrospray Ionization High-Field Asymmetric Waveform Ion Mobility Spectrometry—Mass Spectrometry, Anal. Chem. 1999, 71, 2346-2357.

Miller, R. A., et al., A Novel Micromachined High-Field Asymmetric Waveform-Ion Mobility Spectrometer, Sensors and Actuator B 67, 2000, 300-306.

Guevremont, Roger, High-Field Asymmetric Waveform Ion Mobility Spectrometry: A New Tool for Mass Spectrometry, Journal of Chromatography A, 1058, 2004, 3-19.

(Continued)

*Primary Examiner* — Jack Berman
(74) *Attorney, Agent, or Firm* — James D. Matheson (57) ABSTRACT

A differential ion mobility spectrometry or field asymmetric waveform ion mobility spectrometry (FAIMS) platform is disclosed that utilizes both gas flow and electric field, consecutively or simultaneously, to move ions through the analytical gap. The consecutive combination of flow and field enables rapid and flexible switching of the FAIMS stage "on" (for ion separation) and "off" (for high non-selective transmission) with no hardware modifications. This capability is needed for effective use of multidimensional instrument systems that couple FAIMS to mass spectrometry and/or conventional ion mobility spectrometry. The joint application of flow and field allows controlling the discrimination against high-mobility ions, maximizing it to remove the chemical noise or minimizing it to make the analyses of complex samples more predictable and uniform.

12 Claims, 8 Drawing Sheets

OTHER PUBLICATIONS

Shvartsburg, Alexandre A., et al., High-Resolution Field Asymmetric Waveform Ion Mobility Spectrometry Using New Planar Geometry Analyzers, Anal. Chem. 78, 2006, 3706-3714.

Nazarov, Erkinjon G., et al., Pressure Effects in Differential Mobility Spectrometry, Anal. Chem. 78, 2006, 7697-7706.

Shvartsburg, Alexandre A., Scaling of the Resolving Power and Sensitivity for Planar FAIMS and Mobility-Based Discrimination in Flow- and Field-Driven Analyzers, J. Am. Soc. Mass Spectrom, 18, 2007, 1672-1681.

Kwasnik, Mark, et al., Performance, Resolving Power, and Radial Ion Distributions of a Prototype Nanoelectrospray Ionization Resistive Glass Atmospheric Pressure Ion Mobility Spectrometer, Anal. Chem. 79, 2007, 7782-7791.

Shvartsburg, Alexandre A., et al., Distortion of Ion Structures by Field Asymmetric Waveform Ion Mobility Spectrometry, Anal. Chem. 79, 2007, 1523-1528.

Shvartsburg, Alexandre A., et al., Optimum Waveforms for Differential Ion Mobility Spectrometry (FAIMS), J. Am. Soc. Mass Spectrom. 19, 2008, 1286-1295.

Shvartsburg, Alexandre A., et al., Fundamentals of Traveling Wave Ion Mobility Spectrometry, Anal. Chem. 80, 2008, 9689-9699.

Mabrouki, Ridha, et al., Improving FAIMS Sensitivity Using a Planar Geometry with Slit Interfaces, J. Am. Soc. Mass Spectrom. 20, 2009, 1768-1774.

Shvartsburg, Alexandre A., Differentioal Ion Mobility Spectrometry: Nonlinear Ion Transport and Fundamentals of FAIMS, CRC Press, Boca Raton, FL, 2008, p. 542.

Meek, J. M. et al., Electrical Breakdown of Gases, John Wiley & Sons, Ltd., New York, NY, 1978, p. 145.

* cited by examiner

PLATFORM FOR FIELD ASYMMETRIC WAVEFORM ION MOBILITY SPECTROMETRY WITH ION PROPULSION MODES EMPLOYING GAS FLOW AND ELECTRIC FIELD

CROSS REFERENCE TO RELATED APPLICATION

This application claims priority from Provisional application No. 61/146,795 filed 23 Jan. 2009, incorporated in its entirety herein by reference.

STATEMENT REGARDING RIGHTS TO INVENTION MADE UNDER FEDERALLY-SPONSORED RESEARCH AND DEVELOPMENT

This invention was made with Government support under Contract DE-AC06-76RLO1830 awarded by the U.S. Department of Energy. The Government has certain rights in the invention.

FIELD OF THE INVENTION

The invention is in the field of ion mobility spectrometry (IMS), specifically differential IMS or field asymmetric waveform IMS (FAIMS) and hybrid analytical platforms involving this method.

BACKGROUND OF THE INVENTION

Figure 1A:
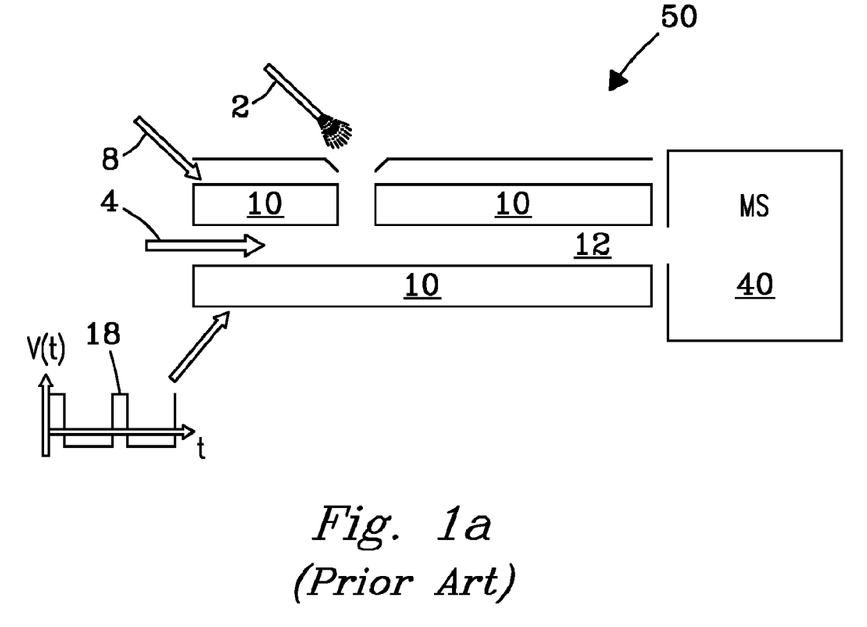
FIGS. 1a-1b (Prior Art) show FAIMS stages that propel ions through the gap using a gas flow (1a) or an electric field (1b).
Figure 1B:
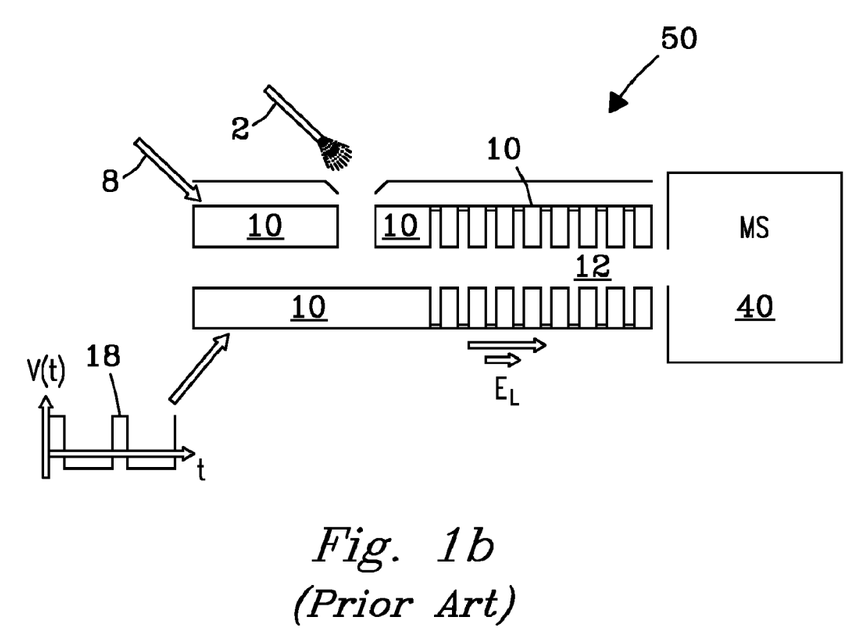

In Field asymmetric waveform ion mobility spectrometry (FAIMS), also termed differential mobility spectrometry (DMS), ions are separated in gases by the difference of mobility at two substantially unequal electric field intensities, E (R. Guevremont. *J. Chromatogr. A* 2004, 1058, 3). The gas pressure is typically ambient (atmospheric), though operation at reduced pressure is possible and may be advantageous (E. G. Nazarov, S. L. Coy, E. V. Krylov, R. A. Miller, G. A. Eiceman. *Anal. Chem.* 2006, 78, 7697). FIG. 1a shows a flow-driven FAIMS stage 50, where ions are filtered in the analytical gap 12 between two electrodes 10, one carrying a periodic asymmetric high-voltage waveform V(t) 18 with the amplitude termed the "dispersion voltage" (DV) and the same or other electrode carrying a fixed "compensation voltage" (CV) 8. At any given CV, only species with a particular difference between the mobility at "high" and "low" E in the positive and negative V(t) segments remains in equilibrium and is most likely to pass the gap. In the FAIMS systems reduced to practice so far, ions are moved through the gap by a steady laminar flow of carrier gas 4. Besides stand-alone use, FAIMS is increasingly employed to filter ions prior to mass spectrometry (MS) and/or drift tube ion mobility spectrometry (DTIMS) analyses (R. W. Purves, R. Guevremont. *Anal. Chem.* 1999, 71, 2346; K. Tang, F. Li, A. A. Shvartsburg, E. F. Strittmatter, R. D. Smith. *Anal. Chem.* 2005, 77, 6381). Ions can be propelled through the gap by a relatively weak electric field ($E_L$) along it instead of the flow (U.S. Pat. No. 7,456,390, U.S. Pat. No. 7,547,879). In FIG. 1b, such a longitudinal field-driven FAIMS stage 50 is shown with $E_L$ along the analytical gap 12 established by segmenting both electrodes 10 and applying a voltage ladder to the segments. Alternatively, the field $E_L$ may be created by maintaining a voltage drop across contiguous electrodes with substantial ohmic resistance, as is known in the art of DTIMS (M. Kwasnik, K. Fuhrer, M. Gonin, K. Barbeau, F. M. Fernandez. *Anal. Chem.* 2007, 79, 7782) and has been considered for FAIMS (U.S. Pat. No. 7,498,570).

As a filtering technique, FAIMS inherently involves ion losses. Hence, to maximize the sensitivity of multidimensional analytical platforms comprising FAIMS, one needs to switch it "off", i.e., to employ the other stage(s) without FAIMS filtering. In particular, the ability to use FAIMS/MS systems for MS-only analyses is usually desired. As FAIMS normally precedes MS or other stage(s) in hybrid systems, this means effectively transmitting ions to those stage(s) through or around the FAIMS unit. In the current art, effective use of such other stage(s) without FAIMS requires physically removing the FAIMS unit and reassembling the instrument in a new configuration. This process calls for trained personnel, testing, and recalibration of the instrument after each insertion or removal of a FAIMS stage, at a substantial cost in time and resources. Ions still pass FAIMS with the asymmetric waveform and CV switched off, but the transmission is poor because of large losses due to diffusion and Coulomb repulsion in a narrow analytical gap. Such losses decrease the sensitivity of instrument platforms without FAIMS, typically to unacceptable levels. Accordingly, there is a need for capability to switch off the FAIMS separation in hybrid platforms without significantly diminishing the instrument sensitivity.

In flow-driven FAIMS, all species traverse the gap in the same time defined by the flow speed and gap length. As the low-field (isotropic) diffusion coefficient of an ion $D_0$ is proportional to mobility K by the Einstein law, species with higher K values diffuse faster and thus spread farther in equal time. Second, more mobile ions further experience stronger field heating that increases the diffusion coefficient, and especially its longitudinal component $D_{II}$ (along the separation field) that determines ion loss on electrodes, above $D_0$. Third, as the amplitude of ion oscillation in the V(t) cycle also scales with K, more mobile species undergo wider oscillations that effectively constrain the gap. These three factors add to a pronounced discrimination against more mobile ions, which are preferentially lost in a gap of any geometry. This is unrelated to the discrimination based on the K(E) form that occurs in curved gaps only (A. A. Shvartsburg, R. D. Smith. *J. Am. Soc. Mass Spectrom.* 2007, 9, 1672). This effect distorts the FAIMS spectra, complicating quantification, affecting the measured isomer abundances, and reducing the sensitivity and reliable dynamic range. Same effect decreases the FAIMS resolution for less mobile species, resulting in a non-uniform and sub-optimum resolving power over a spectrum. For a complex sample that comprises ions with a wide range of K, the discrimination may be severe enough to suppress more mobile species below the detection limit, precluding their observation in FAIMS, and prevent the resolution of different less mobile species that could otherwise be separated. As FAIMS is applied to increasingly complex proteomic and other biological samples that include more diverse species, the issue of mobility discrimination becomes more topical.

In field-driven FAIMS, the ion residence time in the gap ($t_{res}$) scales as 1/K and more mobile ions exit the gap faster. This offsets the proportionality of $D_0$ to K such that all ions would experience identical diffusional broadening at the FAIMS exit (assuming isotropic diffusion), but not the other two factors that contribute to the mobility-based discrimination in flow-driven FAIMS as described above. Therefore, the transition from flow- to field-driven FAIMS should ameliorate, but not eliminate, the generally unwanted suppression of ions with higher K values (A. A. Shvartsburg, R. D. Smith. *J. Am. Soc. Mass Spectrom.* 2007, 9, 1672). The remaining discrimination, still significant in simulations, will be adverse to many applications. Accordingly, one would desire a FAIMS system that reduces this discrimination further.

SUMMARY OF THE INVENTION

The invention is a system for separation, identification, and/or detection of gas-phase ions that includes, as the only or one of the analytical stages, field asymmetric waveform ion mobility spectrometry (FAIMS). The key novelty is that ions are moved through the FAIMS gap using the flow and field drive combined (i) consecutively or (ii) simultaneously to achieve non-obvious benefits not provided by either drive alone. With (ii), the field and flow may pull ions in the same or opposite directions.

One goal of the invention is providing a method for effective, rapid, and convenient switch-off of the FAIMS separation in hybrid platforms, to enable more sensitive analyses using the other stage(s) by limiting ion losses in the FAIMS gap. This is achieved by accelerating ion transit through the gap in the "off" mode compared to the "on" mode, where a minimum $t_{res}$ is determined by the desired resolution (A. A. Shvartsburg, R. D. Smith. *J. Am. Soc. Mass Spectrom.* 2007, 9, 1672). The acceleration is obtained by applying electric field $E_L$ along the gap in the "off" mode with V(t) and CV absent, alone or in addition to the flow moving ions in the same direction as the field. The direction of flow (if any) coincides with $E_L$ for cations and is opposite for anions. The field may be constant, such as used in DTIMS and described in the art for field-driven FAIMS, or time-dependent, e.g., a "traveling wave" similar to that used in traveling-wave IMS (TWIMS) to disperse ions by the absolute mobility (A. A. Shvartsburg, R. D. Smith. *Anal. Chem.* 2008, 80, 9689).

Instrument stages, if any, coupled to FAIMS include, but are not limited to, e.g., mass spectrometry (MS) in implementations such as quadrupole, ion trap, Fourier transform ion cyclotron resonance (FTICR), orbitrap, or time-of-flight; ion mobility spectrometry (IMS) based on the absolute K values in DTIMS, TWIMS, differential mobility analyzers (DMA), or other implementations; spectroscopies such as photoelectron, photodissociation, X-ray, or other spectroscopies; surface analysis or ion deposition stages, and combinations of these and other stages. These stages are usually subsequent to the FAIMS step, but may equally precede it within the scope of the invention.

In one embodiment, the stage subsequent to FAIMS is MS (or conventional IMS at sub-ambient gas pressure followed by MS), with FAIMS configured for FAIMS/MS or MS-only operation (or for FAIMS/IMS/MS or IMS/MS operation, respectively). Here, FAIMS may work at ambient or sub-ambient pressure. In the latter case, the FAIMS stage may be located inside the MS (or IMS) system enclosure, i.e., behind the MS (or IMS) inlet such as a heated capillary or curtain plate/orifice interface. The sub-ambient pressure preferably ranges from ~0.1 to 1 atm, but may be lower to ~0.01 atm, depending on the requirements for FAIMS resolving power and scan speed.

FAIMS stages known in the art commonly have planar or transverse ("side-to-side") cylindrical geometry (U.S. Pat. No. 7,223,967). These and some other designs such as "hooked" (U.S. Pat. No. 7,491,930) permit free lateral spread of ions due to diffusion and/or Coulomb repulsion, thus the ion beams approaching the exit are ribbon-like with a rectangular cross-section. With any pressure in FAIMS, the transmission of ions from the exit of such units to subsequent stages at lower pressure is maximized by using (at the conductance limit) a slit-shaped aperture with the cross-sectional shape matching that of the beam as closely as possible (U.S. Pat. No. 7,339,166). Such slit interfaces can be employed to couple the FAIMS units to subsequent lower-pressure stages such as MS or conventional IMS (R. Mabrouki, R. T. Kelly, D. C. Prior, A. A. Shvartsburg, K. Tang, R. D. Smith. *J. Am. Soc. Mass Spectrom.* 2009, 20, 1768). Ribbon-shaped ion beams coming from slit apertures may be re-focused to circular cross sections using one or more electrodynamic ion funnels (U.S. Pat. No. 6,107,628). If the pressure in FAIMS is low enough for effective funnel operation, those beams may be focused by a funnel directly, with no conductance limit between the FAIMS unit and the funnel.

Another goal of the invention is to control the mobility-based discrimination in FAIMS, which is inevitable with either the flow drive or (to a lesser extent) field drive alone. The discrimination in planar gaps for ions of interest is minimized by applying a flow of specific speed to push ions in the direction opposing their drift in the longitudinal field $E_L$, though the field prevails and ions traverse the gap under its control. Here, the field and flow directions are opposite for cations and coincide for anions, and the optimum flow velocity depends on $E_L$ and the mobility of ions of interest. Common ion sources such as electrospray ionization (ESI) and matrix-assisted laser desorption ionization (MALDI) produce intense background ions, which impede the analysis of target ions and thus are best removed as early as possible. Interfering ions are mostly solvent or matrix clusters that are often smaller and thus more mobile than the target analytes. Thus the mobility-based discrimination in FAIMS may suppress the chemical noise and is beneficial in some scenarios. Then the discrimination in planar gaps may be maximized by again applying flow and field $E_L$ that seek to move ions in opposite directions, but now with the flow prevailing and carrying ions of interest through the gap.

In summary, the invention combines the longitudinal electric field (drive) and gas flow (drive) in FAIMS to achieve analytical benefits impossible with either drive alone. In particular, consecutive application of the flow and field drives allows a FAIMS/MS instrument to toggle between the FAIMS/MS and MS-only mode without mechanical modifications. With FAIMS on, the field drive is disabled and ions are moved through the gap by flow only. With FAIMS off, the asymmetric waveform and compensation voltage are removed and the field drive is on. The combination of field and flow rapidly moves ions through the gap, minimizing their loss to electrodes. Then FAIMS can be easily switched on and off on the software level, with no hardware changes. Further, propelling ions through FAIMS using the field and flow drives together allows one to control and minimize mobility-based discrimination of ions in units of any geometry.

The purpose of the foregoing abstract is to enable the United States Patent and Trademark Office and the public, especially the scientists, engineers, and practitioners in the art not familiar with the patent or legal phraseology, to quickly grasp the essence of the technical disclosure of the application. The abstract is intended neither to define the instant invention that is measured by the claims, nor to limit its scope in any way.

Various advantages and novel features of the present invention are described herein and will become readily apparent to those skilled in the art from the following detailed description. In the preceding and following descriptions, the various embodiments, including the preferred embodiments and the best mode contemplated for carrying out the invention, have been shown and described. As will be realized, those embodiments may be modified in various respects without departing from the invention. Accordingly, the drawings and description of the preferred embodiments set forth hereafter are to be regarded as illustrative, rather than restrictive, in nature. Embodiments of the invention are described below with reference to the following accompanying drawings.

DETAILED DESCRIPTION

The invention solves the problems with flow-driven FAIMS stages known in the art, where major losses of ions during their transmission through the analytical gap: (i) prevent effective use of other instrument stages in hybrid instruments without FAIMS filtering, and (ii) cause significant mobility-based discrimination. In particular, the invention enables operating various platforms comprising FAIMS, such as FAIMS/MS, FAIMS/DTIMS, FAIMS/TWIMS, FAIMS/DTIMS/MS, and FAIMS/TWIMS/MS, with FAIMS "on" or "off". This allows for maximizing the specificity and reducing chemical background (with FAIMS on) and maximizing the sensitivity, throughput, and quantification accuracy without the distortions introduced by FAIMS (with FAIMS off). In another aspect, the invention controls and minimizes mobility-based discrimination of ions in FAIMS.

Asymmetric Waveforms

The waveform profiles for FAIMS include rectangular, bisinusoidal, clipped-sinusoidal, and their derivatives and superpositions (A. A. Shvartsburg, *Differential Ion Mobility Spectrometry*, CRC Press, Boca Raton, Fla., 2008), which reference is incorporated herein in its entirety. In one embodiment, the invention employs an exemplary bisinusoidal V(t), e.g., with a frequency of w=750 kHz. The waveform is produced using a power supply that includes a resonating LC circuit adding, e.g., 750 and 1500 kHz harmonics (at a 2:1 amplitude ratio), as is known in the art. As in other contexts, the present invention would optimally employ a rectangular waveform with appropriate "high-to-low" ratio (A. A. Shvartsburg, R. D. Smith. *J. Am. Soc. Mass Spectrom.* 2008, 19, 1286), but harmonic-based waveforms may be preferred for instrumental reasons.

Figure 2A:
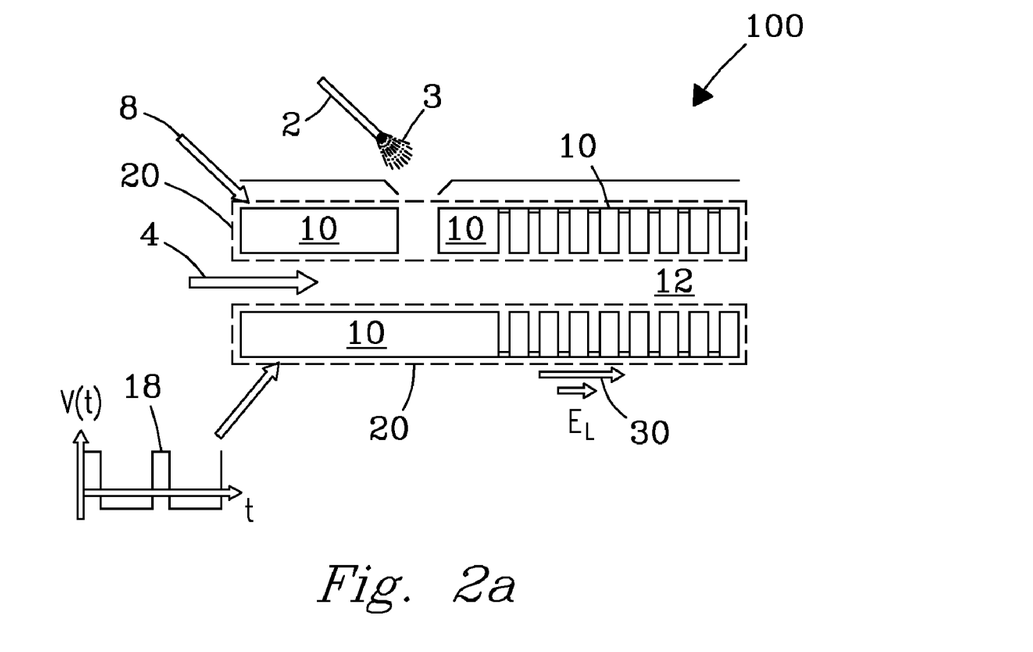
FIGS. 2a-2b show a FAIMS stage that combines field and flow drives, according to an embodiment of the invention.
Figure 2B:
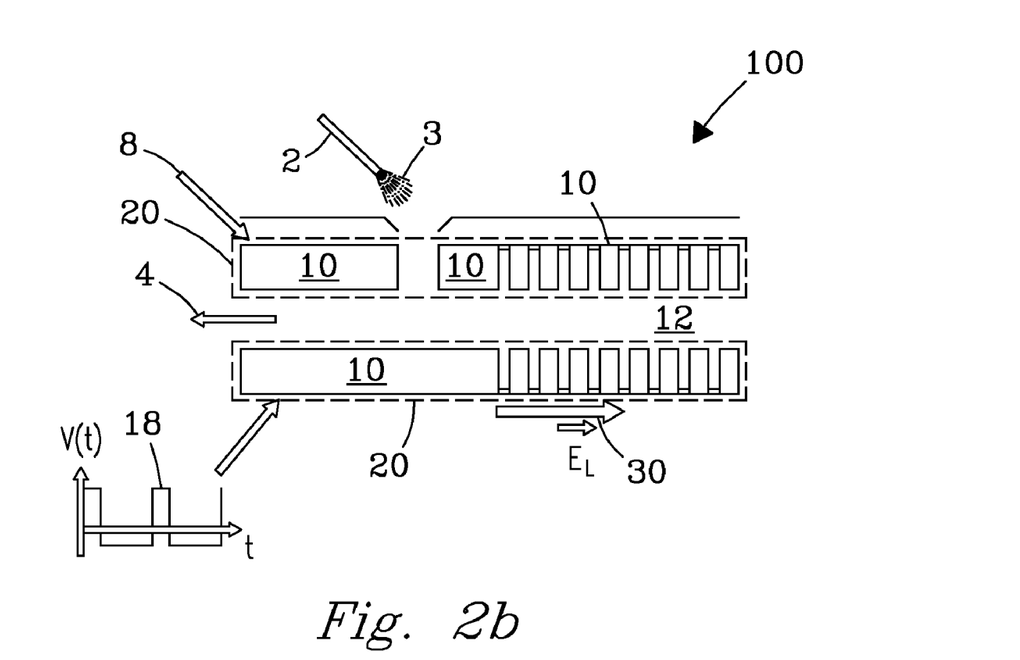

FIGS. 2a and 2b illustrate exemplary FAIMS stages 100. These stages include two planar electrodes 20 composed of segments 10, each electrically insulated from the others so that distinct voltages can be applied to each segment to create a longitudinal field ($E_L$) 30 along the analytical gap 12. An ionization source 2 (e.g., ESI) produces ions 3 that enter gap 12 and are moved through the gap by gas flow drive 4, field drive 30, or both. The term "field drive" means an electric field (constant or time-dependent) that moves ions along gap 12 at a selected velocity. The term "flow drive" means a flow of gas at a certain rate that propels ions through gap 12 at a selected velocity. Movement of ions solely by flow drive 4 or field drive 30 is termed "flow-driven" or "field-driven", respectively. In various embodiments, ions are moved through the gap by a combination of flow 4 and field 30. The two drives can pull ions in the same direction (FIG. 2a) or in opposite directions with the flow slowing the ion drift along the gap, i.e., in a counter-flow regime (FIG. 2b). A fixed longitudinal field 30 may be provided by inserting resistors between all adjacent segments 10 and applying a constant voltage between the first and last segment. The field 30 may also be established by directly addressing some or all segments, which would permit a time-dependent field (e.g., a traveling wave). In an alternative embodiment without segmentation, the FAIMS electrodes 20 or their surface parts facing the gap are made of a resistive material. Field 30 is then created by applying a constant voltage between the electrode termini. All such modifications as will be envisioned by those of ordinary skill in the art in view of the disclosure are within the scope of the invention. No limitations are intended.

The disclosure is not limited to the regime where a field moves ions against counter-flow (FIG. 2b). Instead, a forward flow may carry ions through the gap against a retarding potential gradient seeking to pull them back. Such a forward flow mode may be useful to improve FAIMS resolution by extending the ion residence in the gap. Further, $t_{res}$ would now increase for more mobile ions, augmenting the discrimination against them beyond that with the flow drive only. The species with K values above some cutoff, will be swept back and not pass the gap, amounting to an infinite discrimination. As discussed above, suppression of more mobile (typically small) ions would benefit some applications.

Figure 3A:
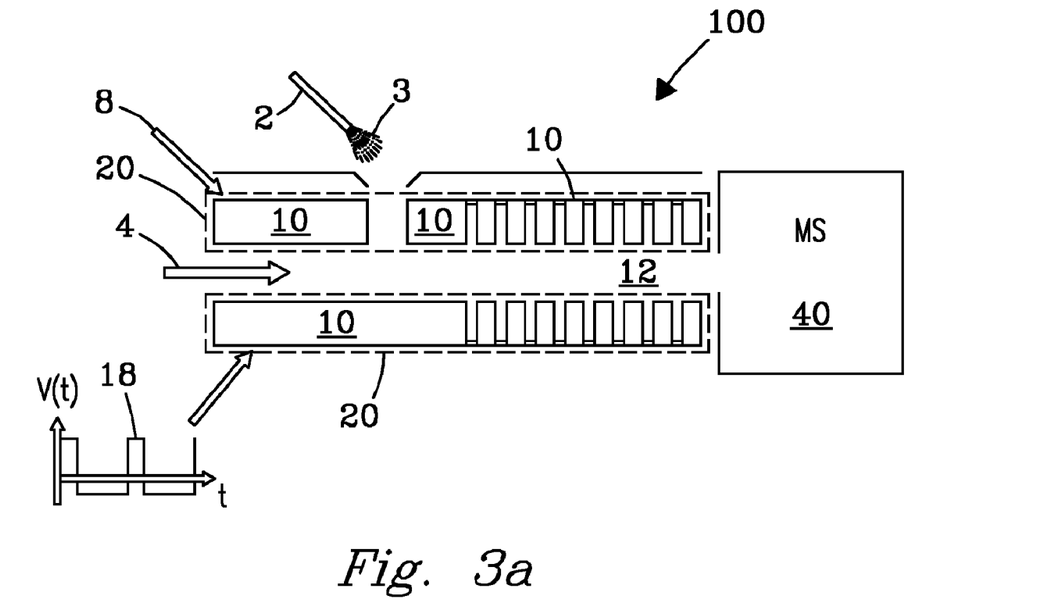
FIGS. 3a-3b show a FAIMS stage coupled to a subsequent instrument stage, according to an embodiment of the invention.
Figure 3B:
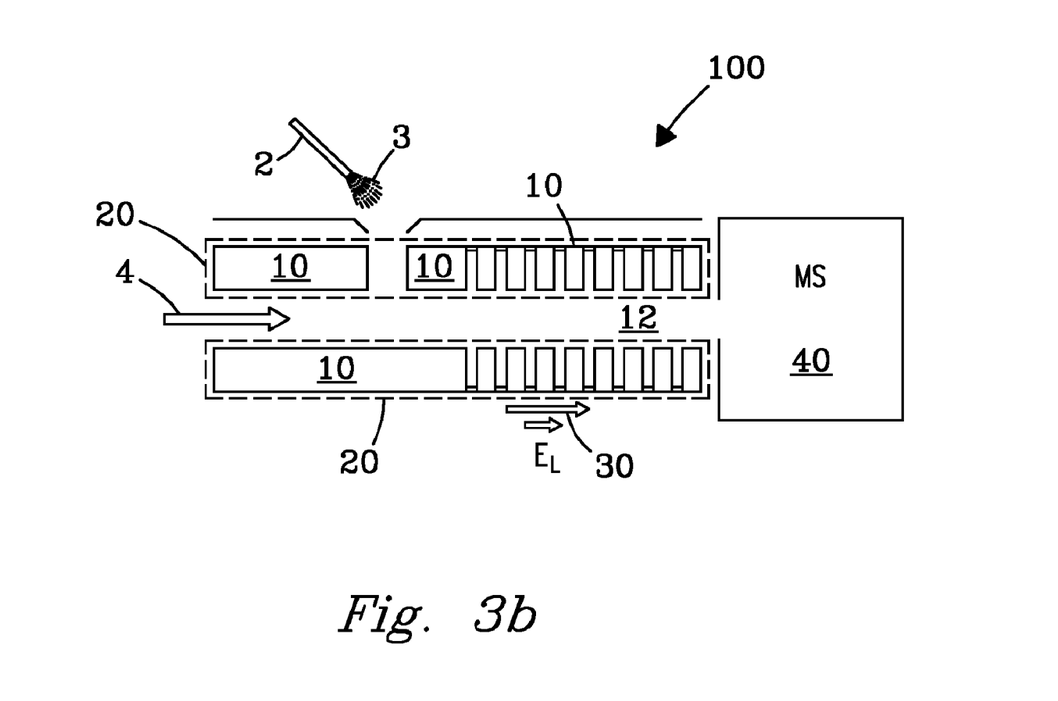

FIGS. 3a and 3b show a FAIMS unit 100 of the invention at ambient pressure, coupled to another instrument stage 40. In the "on" mode (FIG. 3a), the electrodes 20 carry V(t) 18 and CV 8. The longitudinal field 30 along the gap 12 is switched off by applying equal voltages to all segments 10, and only the gas 4 carries ions through the gap. In the "off" mode (FIG. 3b), both V(t) 18 and CV 8 are off. The longitudinal field 30 is switched on to move ions in the same direction as the flow 4. Pulled by both electric field 30 and gas 4, ions traverse the stage 100 substantially faster (e.g., by 10 times compared to "on" mode) to minimize ion losses in the gap 12. While FIGS. 3a and 3b show the FAIMS unit 100 preceding the stage 40 in ion progression through the system, the invention encompasses any order of FAIMS relative to other stage(s), including that subsequent to all of them or preceding some and subsequent to others.

Figure 4A:
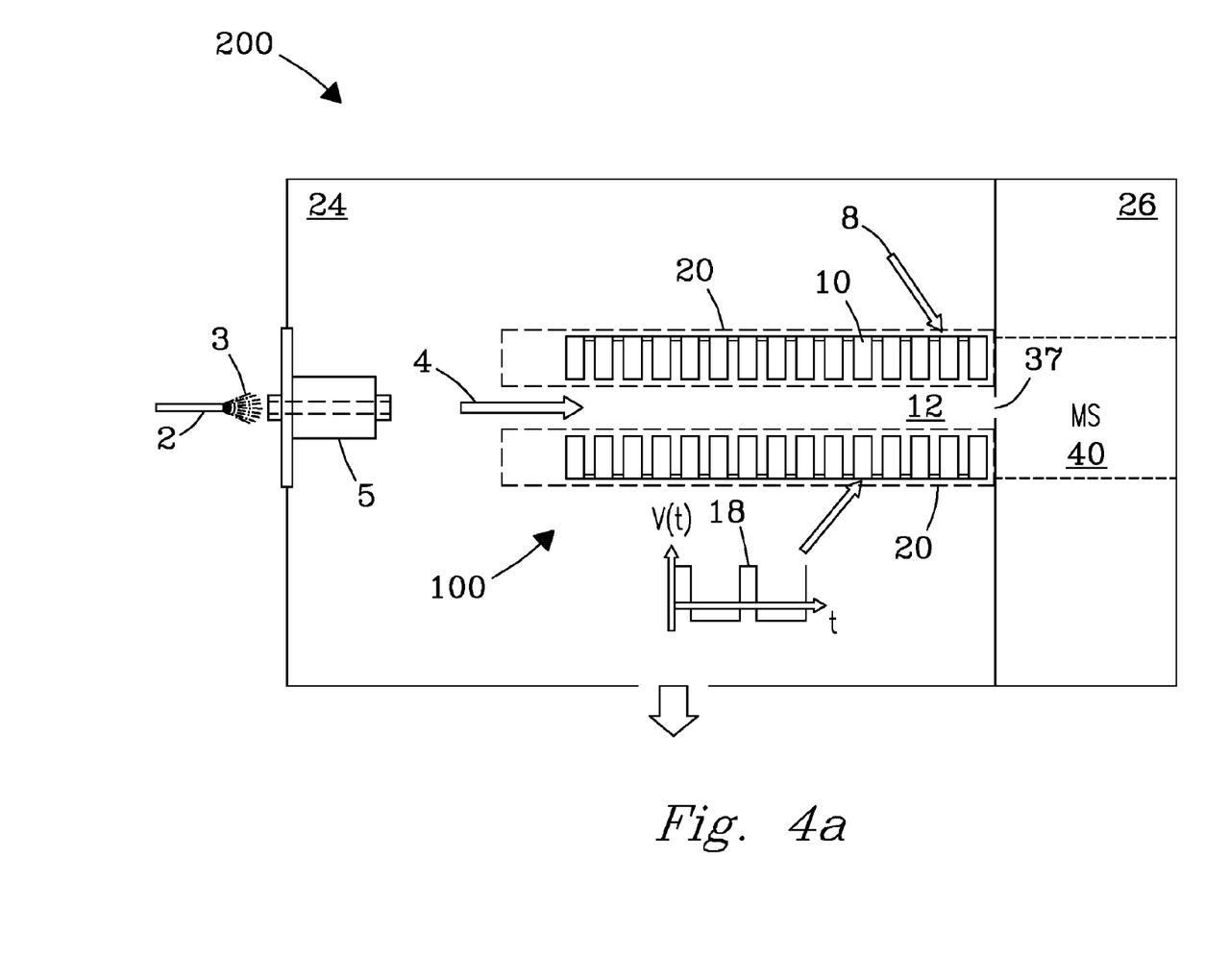
FIGS. 4a-4b show an integrated FAIMS/MS system, according to another embodiment of the invention.
Figure 4B:
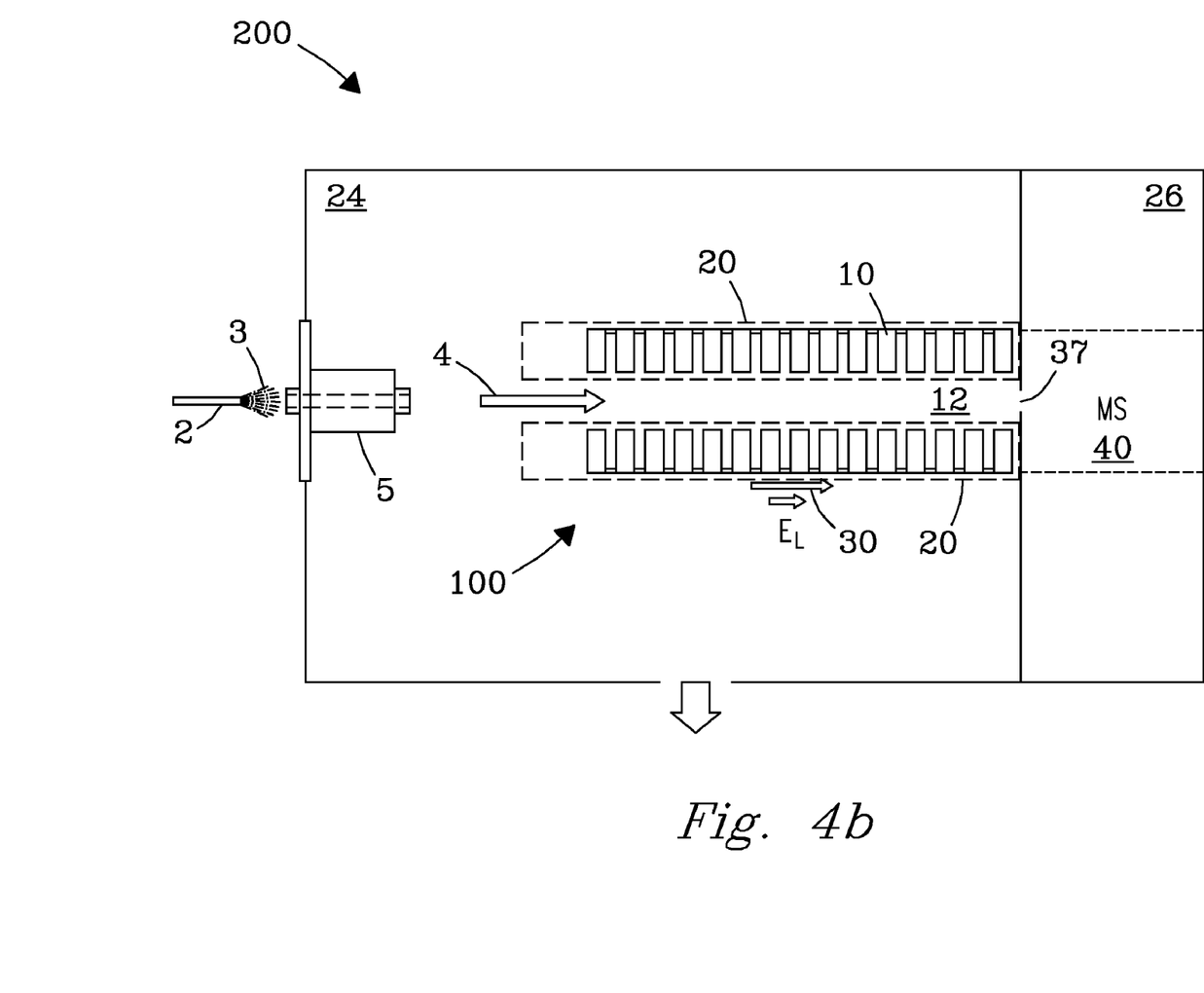

FIGS. 4a and 4b show a FAIMS/MS (or FAIMS/IMS/MS with sub-ambient pressure IMS) system 200, according to another embodiment, that incorporates a FAIMS stage 100 as an integral component of MS (or IMS/MS) platform 40, effecting separation, characterization, or detection of gas-phase ions. System 200 retains optimum instrument sensitivity, and FAIMS can be switched on (FIG. 4a) for FAIMS/MS (or FAIMS/IMS/MS) analyses or off (FIG. 4b) for MS-only (or IMS/MS) analyses without removing stage 100. Here, stage 100 is at sub-ambient pressure, behind the inlet capillary 5 within the first vacuum region 24 of MS (or IMS/MS) platform 40. For optimum ion transmission, the aperture 37 providing the conductance limit from FAIMS stage 100 to the following stage 26 at a lower pressure may be slit-shaped, depending on the FAIMS unit geometry. In other aspects, the FAIMS operation in "on" and "off" modes copies that at the ambient pressure, described with reference to FIGS. 3a and 3b using the same nomenclature.

Figure 5A:
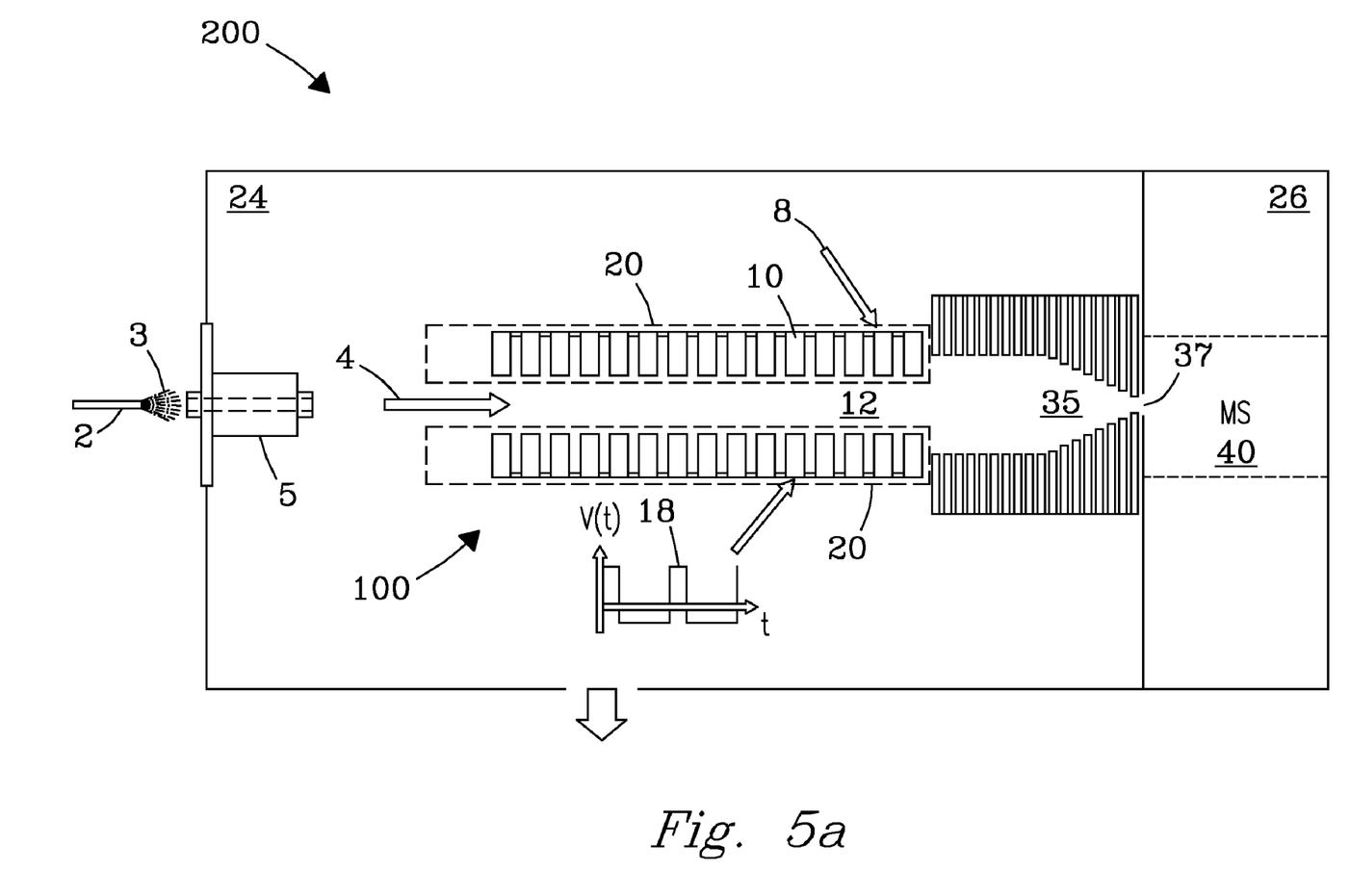
FIGS. 5a-5b show an integrated FAIMS/MS system, according to yet another embodiment of the invention.
Figure 5B:
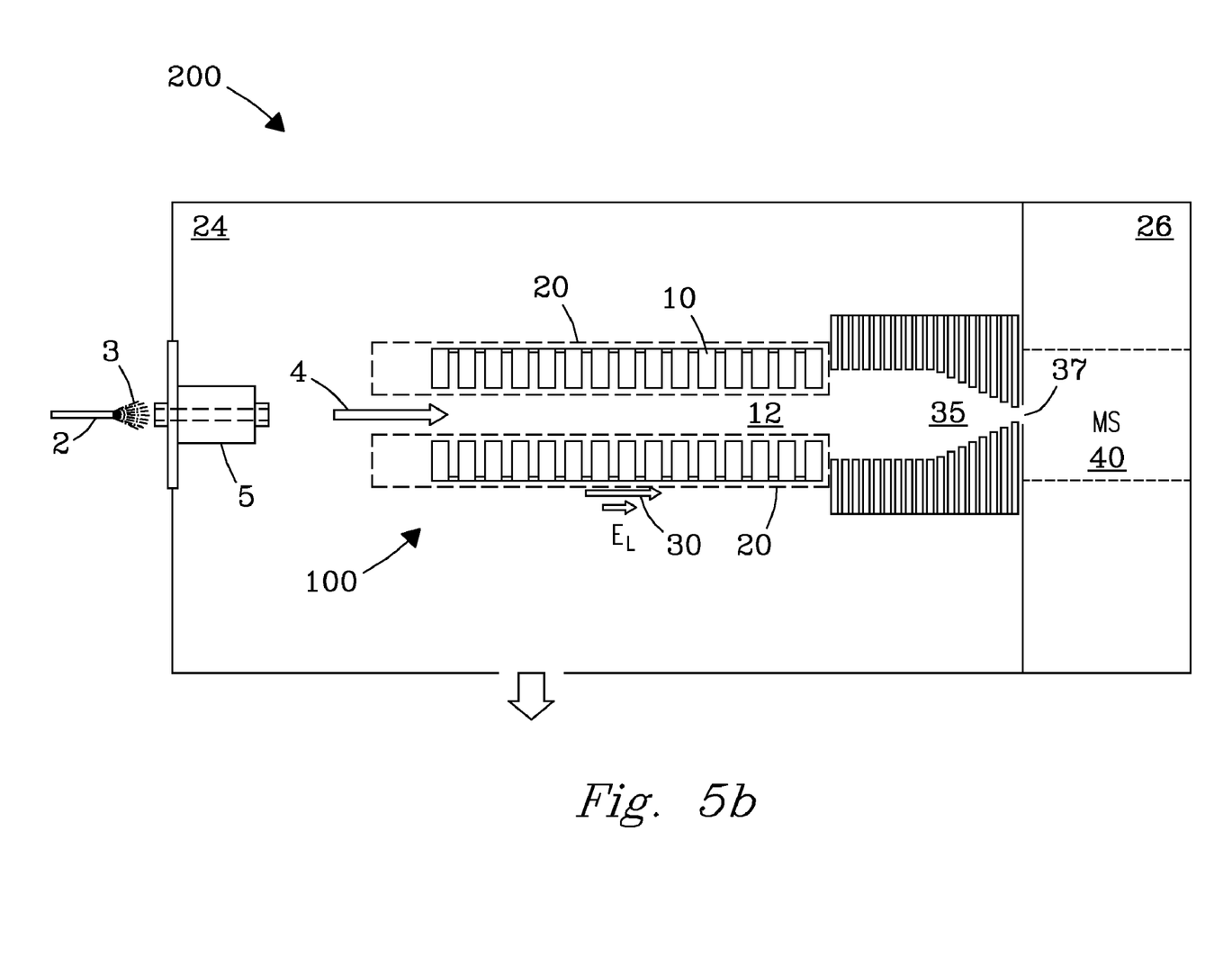

FIGS. 5a and 5b show still yet other embodiment for an integrated FAIMS/MS (or FAIMS/IMS/MS with sub-ambient pressure IMS) system 200. Here, FAIMS stage 100 is interfaced to the following vacuum stage 26 using an electrodynamic ion funnel 35, though a slit or aperture of another shape may still be placed after the FAIMS exit (as in FIG. 4a) prior to the funnel, depending on the pressure in the FAIMS and funnel regions. In other aspects, the FAIMS operation in "on" and "off" modes is as described previously with reference to FIGS. 4a and 4b using the same nomenclature.

In its first aspect, the invention hinges on the realization that switching the FAIMS stage "off" in hybrid platforms by simply accelerating the flow is less effective and convenient than the present solution. With the flow drive only, the residence time $t_{res}$ is proportional to the inverse flow speed. As high ion transmission through the gap requires a major reduction of $t_{res}$ compared to that necessary for effective FAIMS separation, switching FAIMS "off" without unacceptable ion losses would involve drastic flow acceleration. This would cause severe losses at the interface of FAIMS to subsequent lower-pressure stages such as MS or sub-ambient pressure IMS (because of the mismatch between the increased outflow from FAIMS and limited gas conductance to those stages), unless the conductance and the pumping capacity of these stages are raised to the higher FAIMS flow level. However, such increase of the pumping capacity is generally impractical, and the higher inlet conductance would not match the reduced outflow from FAIMS switched "on", causing other problems. Further, the electrode voltages and thus field $E_L$ can be manipulated faster than the flow by orders of magnitude, allowing far more rapid and flexible toggling between the "on" and "off" modes. In the second aspect of the invention, controlling and reducing the mobility-based discrimination requires a combination of field and flow drives. Switching FAIMS on/off or adjusting the mobility-based discrimination may be enabled in the instrument control software. In particular, the invention allows rapid manual or automatic toggling between the "on" and "off" modes. Such toggling may be carried out in a data-dependent manner, depending on the measured signal intensity (e.g., with FAIMS switched "off" if the signal overall or in a particular m/z region in MS falls below a pre-set threshold) or spectral properties (e.g., with FAIMS switched "on" if the spectral complexity exceeds a certain level).

Longitudinal Field Intensity for Effective "FAIMS-Off" Operation

The magnitude of $E_L$ for effective ion transmission with FAIMS "off" can be estimated from the required reduction of $t_{res}$ compared to the "on" mode. For optimum resolution/sensitivity balance, planar FAIMS can transmit ~10-20% of ions (at peak CV). Then, a near-100% transmission would require reducing $t_{res}$ by an order of magnitude, e.g.: (i) from ~150 to ~15 ms in a "full-size" FAIMS device with a ~2 mm wide gap (A. A. Shvartsburg, F. Li, K. Tang, R. D. Smith. *Anal. Chem.* 2006, 78, 3706), or (ii) from ~3 ms to ~0.3 ms in a miniaturized device with ~0.5 mm gap (R. A. Miller, G. A. Eiceman, E. G. Nazarov, A. T. King. *Sens. Actuat. B* 2000, 67, 300). This means increasing the longitudinal ion velocity by the same factor of 10, i.e., (i) from ~0.33 m/s (~5 cm gap length traversed in ~150 ms) to ~3.3 m/s, or (ii) from ~5 m/s (~1.5 cm gap length traversed in ~3 ms) to ~50 m/s. With an unchanged gas flow, the drift ion velocity (in the longitudinal field) should be 9× flow velocity, i.e., 3 m/s in (i) or 45 m/s in (ii). Typical ions of interest generated by ESI sources 2 have K ~1-2 $cm^2$/(Vs) in $N_2$ or air at ambient temperature and pressure. Thus, achieving the above drift velocities requires an $E_L$ of ~150-300 V/cm in (i) and ~2.2-4.5 kV/cm in (ii). A somewhat higher or lower $E_L$ may be optimum when looking at species with K<1 or >2 $cm^2$/(Vs), respectively. In any event, the needed $E_L$ values are well within the range of dispersion fields normally created by waveform 18 (~20-30 kV/cm) and thus can be established without interfering with FAIMS separation across the gap 12, or field heating of ions significantly beyond that at the V(t) peak (A. A. Shvartsburg, F. Li, K. Tang, R. D. Smith, *Anal. Chem.* 2007, 79, 1523). From the engineering perspective, in (i), setting the maximum $E_L$=300 V/cm over a 5-cm long gap 12 requires a voltage drop of 1.5 kV, which is reasonable given the typical DV ~4-5 kV. If the longitudinal field 30 is created using segmented electrodes and the segments are 1-mm long (the maximum reasonable for 2 mm gap width), the voltage ladder steps would be ~30 V, or well under the breakdown threshold of ~200 V for any distance in ambient air or $N_2$ (J. M. Meek, J. D. Craggs. *Electrical Breakdown of Gases.* Wiley, NY, 1978).

Figure 6:
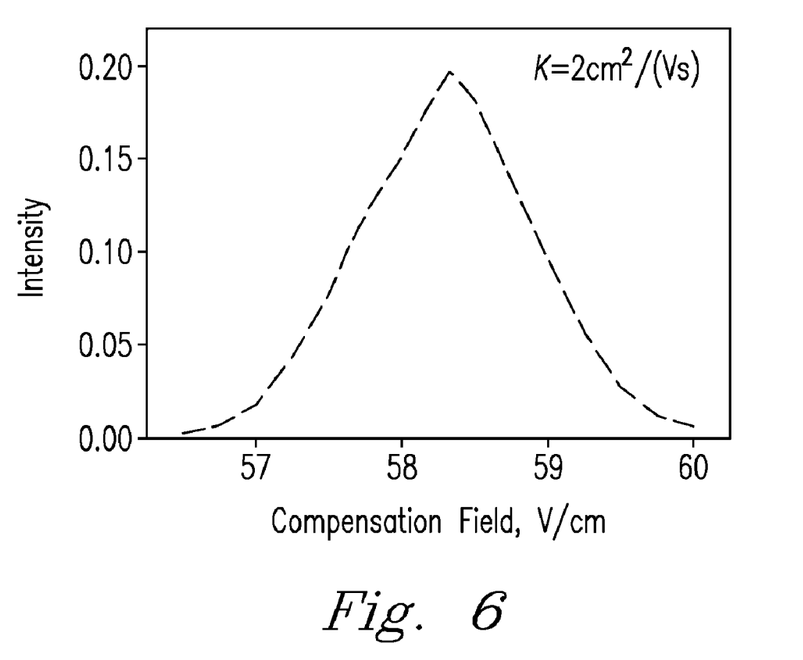
FIG. 6 shows a peak profile simulated for a singly-charged ion.
Figure 7:
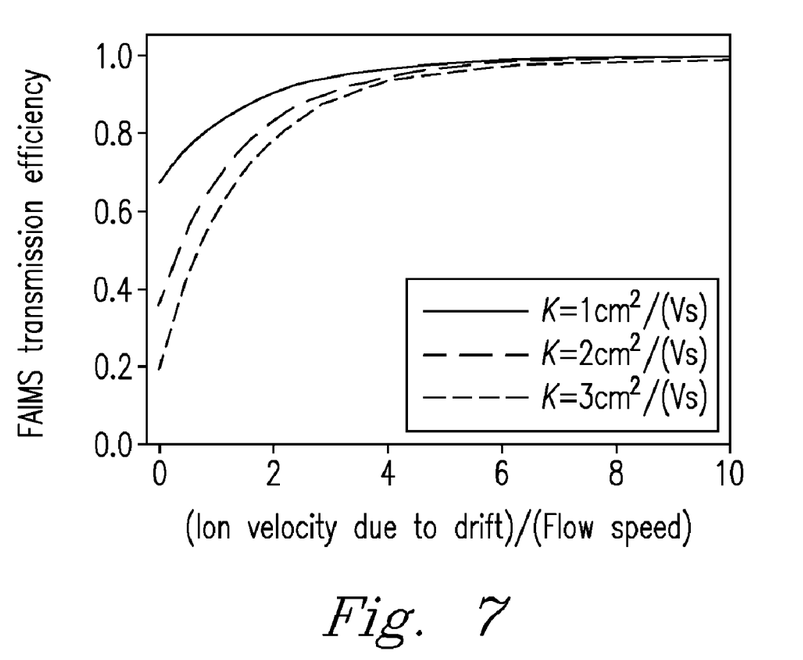
FIG. 7 shows a calculated transmission efficiency through a FAIMS stage in the "off" mode for ions over a range of mobility, as a function of ion drift velocity due to longitudinal field relative to the flow speed.

FIGS. 6 and 7 present simulation results for an exemplary "on/off FAIMS" stage of the invention, featuring planar electrodes 10, a gap 12 of 2 mm width, a bisinusoidal V(t) with w=750 kHz and DV=4 kV, a flow drive 4 (in the "on" mode), and $t_{res}$=100 ms. FIG. 6 shows the peak profile for a (1+) ion with K=2 $cm^2$/(Vs) in $N_2$ gas, with the coefficient ($\alpha_2$) in the K(E) expansion equal to 0.86E-10 $(cm/V)^2$. FIG. 7 shows the transmission efficiency for exemplary ions with K=1, 2, and 3 $cm^2$/(Vs) through the gap with FAIMS "off", as a function of the ratio of the ion drift velocity (due to longitudinal field 30) to the speed of flow 4. These results demonstrate that accelerating the ion transit tenfold when FAIMS is off virtually eliminates ion losses, even for the most mobile species with fastest diffusion. A more modest acceleration by ~5 times still produces >90% transmission in all cases while halving the needed $E_L$, perhaps a reasonable compromise between the transmission efficiency and expense of establishing the longitudinal field.

Controlling and Minimizing Mobility-Based Discrimination

Flow-driven FAIMS discriminates against ions of higher mobility for the three reasons stated in the introduction. This is especially consequential in global analyses, where the K values of actual or potentially present species may differ by up to ~5 times (A. A. Shvartsburg, R. D. Smith. *J. Am. Soc. Mass Spectrom.* 2007, 9, 1672). As described herein, the field drive removes only the first factor contributing to the effect, and high-K ions are still discriminated against. The present invention teaches reducing the remaining discrimination by applying a counter-flow 4 that retards the ion drift through FAIMS caused by field 30. Such counter-flow increases $t_{res}$ for all ions, but more so for less mobile ions $t_{res}$ that drift slower. For example, in a 7-cm long gap 12, achieving 100 ms and thus a longitudinal velocity of 70 cm/s for a species A with K=3 $cm^2$/(Vs) calls for $E_L$=23 V/cm. At the same $E_L$, another species B with K=0.9 $cm^2$/(Vs) drifts with a velocity of only 21 cm/s. A counter-flow 4 with linear speed of 5 cm/s will diminish the net transit velocity and thus raise $t_{res}$ by 8% for A but 31% for B. The effect of counter-flow obviously increases at higher flow speeds. With common operating parameters (e.g., a 2 mm gap and bisinusoidal waveform with w=750 kHz), eliminating the residual discrimination in field-driven FAIMS between A and B requires increasing $t_{res}$ for the latter by ~50% relative to the former. In the above scenario, this would happen at the flow speed of 8 cm/s, with the net transit velocity reduced by 12% (i.e., to 62 cm/s) for A, but by 62% (i.e., to 13 V/cm) for B. A counter-flow limits analyses to ions with K exceeding some threshold that corresponds to the zero net transit velocity: less mobile species are swept back through the gap and not observed. At the above flow speed of 8 cm/s, that threshold is K ~0.3 cm$^2$/(Vs). In practice, nearly all species generated by ESI have greater K values, and the lower K limit is not a major analytical impediment. Thus, no limitations are intended.

Besides the advantage of counter-flow for reducing the mobility-based discrimination in FAIMS, it may also provide a substantial benefit of sweeping the neutral species (e.g., arising from the ESI solvent vapor) out of the analytical gap and preventing them from entering subsequent stages such as MS. As is known in the art of DTIMS, removal of neutral contaminants from the IMS volume suppresses the ion-molecule clustering and charge exchange between ions and neutrals. These precautions often improve sensitivity by preventing the loss of analyte ions to those reactions and preclude the emergence of artifact features reflecting the products.

While a number of embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A method for separation, characterization, and/or detection of gas-phase ions, comprising differential ion mobility spectrometry or FAIMS and other methods, characterized by the step of:
  applying, with the FAIMS separation disabled in the absence of an asymmetric waveform and a compensation voltage, a longitudinal electric field alone or in addition to the gas flow to change the ion residence time in the FAIMS gap to increase the ion transmission through said gap or to modify the selectivity of the ion transmission.

2. The method of claim 1, wherein the flow and field drives propel ions in one direction, with the flow and drift velocities adding to a higher ion transit velocity through the gap, thereby reducing the ion residence time and losses inside the gap.

3. The method of claim 1, wherein said flow is directed along the ion path through the system, and said field seeks to pull ions back toward the source, thereby increasing discrimination against more mobile species and preventing those with mobility above a selected threshold from passing the gap.

4. The method of claim 1, wherein said field is directed along the ion path through the gap, and said flow seeks to pull ions back toward the source, thereby decreasing discrimination against more mobile species and removing neutral contaminants from the gap.

5. The method of claim 1, wherein said field is time-dependent.

6. The method of claim 1, wherein enabling or disabling FAIMS separation requires no mechanical modifications.

7. The method of claim 1, wherein said other method(s) is selected from the group consisting of mass spectrometry (MS), ion mobility spectrometry (IMS), spectroscopy, surface analysis, ion deposition methods, and combinations thereof.

8. The method of claim 1, further comprising the step of electrodynamically focusing ions exiting FAIMS for injection into a subsequent stage(s).

9. The method of claim 1, wherein the gas pressure in FAIMS is sub-ambient.

10. The method of claim 9, wherein said sub-ambient pressure exceeds 0.01 atm.

11. The method of claim 9, wherein FAIMS analysis is immediately followed by analysis using mass spectrometry (MS) or ion mobility spectrometry at sub-ambient pressure.

12. A method for separation, characterization, and/or detection of ions using differential ion mobility spectrometry or FAIMS, comprising:
  simultaneously applying a longitudinal electric field and a gas flow to move ions through the analytical gap of a FAIMS stage, wherein:
  (i) said gas flow is directed along the ion path through the analytical gap and said electric field pulls ions back toward the source thereby increasing discrimination against more mobile species compared to the flow-only regime and preventing those with mobility above a selected threshold from passing through the analytical gap; or
  (ii) the flow and the field are both directed along the ion path through the analytical gap thereby decreasing discrimination against more mobile species compared to the flow-only regime; or
  (iii) the field is directed along the ion path through the analytical gap and said flow pulls ions back toward the source thereby increasing discrimination against less mobile species compared to the field-only regime and preventing those with mobility below a selected threshold from passing through the analytical gap; and
  wherein the field is time-dependent and the gas flow is adjusted relative to the field intensity to minimize mobility-based discrimination over the desired mobility range.

* * * * *